(12) United States Patent  
Marchione (10) Patent No.: US 12,028,589 B2  
(45) Date of Patent: Jul. 2, 2024

(54) COVERING FOR AN ELECTRONIC IMAGING DEVICE

(71) Applicant: Robert L. Marchione, Lebanon, NH (US)

(72) Inventor: Robert L. Marchione, Lebanon, NH (US)

( * ) Notice: Subject to any disclaimer, the term of this patent is extended or adjusted under 35 U.S.C. 154(b) by 772 days.

(21) Appl. No.: 17/027,447

(22) Filed: Sep. 21, 2020

(65) Prior Publication Data

US 2021/0092262 A1  Mar. 25, 2021

Related U.S. Application Data

(60) Provisional application No. 62/902,436, filed on Sep. 19, 2019.

(51) Int. Cl.
| | |
|---|---|
| *H04N 23/51* | (2023.01) |
| *A61B 46/10* | (2016.01) |
| *G06F 1/16* | (2006.01) |

(52) U.S. Cl.
CPC ............ *H04N 23/51* (2023.01); *A61B 46/10* (2016.02); *G06F 1/1607* (2013.01); *G06F 2200/1633* (2013.01)

(58) Field of Classification Search
CPC .................. H04N 23/51; G06F 1/1607; G06F 2200/1633; G06F 1/1626; G06F 1/1656; G06F 1/1628; A61B 46/10
See application file for complete search history.

(56) References Cited

U.S. PATENT DOCUMENTS

| | | | |
|---|---|---|---|
| 4,535,481 A | 8/1985 | Ruth-Larson et al. | |
| 4,963,693 A * | 10/1990 | Kodl | B43L 3/007 |
| | | | 73/431 |
| 5,151,314 A | 9/1992 | Brown | |
| 5,429,142 A * | 7/1995 | Szabo | A61B 46/10 |
| | | | 128/853 |
| 5,743,273 A | 4/1998 | Newman | |
| 5,957,831 A * | 9/1999 | Adair | A61B 1/00052 |
| | | | 600/101 |
| 6,132,367 A * | 10/2000 | Adair | A61B 1/00052 |
| | | | 600/101 |
| 6,659,274 B2 * | 12/2003 | Enners | G06F 1/1626 |
| | | | 206/811 |

(Continued)

*Primary Examiner* — Twyler L Haskins  
*Assistant Examiner* — John H Morehead, III  
(74) *Attorney, Agent, or Firm* — Thomas P. O'Connell; O'Connell Law Firm (57) ABSTRACT

A covering for an electronic imaging device with an optically transparent display screen viewing window centrally disposed in a band bag sleeve to define an inner volume with a mouth. An adherent, such as an optically transparent adhesive, is disposed on an inner surface of the viewing window for adhering to a display screen of the electronic imaging device. A cinching mechanism is operative to constrict the mouth of the band bag sleeve. A sterile barrier is thus created between the electronic imaging device and an exterior environment while permitting optically clear, stable viewing and operation of the display screen. A method for enveloping an electronic imaging device with a covering is founded on providing such a covering, causing the electronic imaging device to be received through the mouth and into the inner volume, and adhering the display screen viewing window to the display screen.

27 Claims, 10 Drawing Sheets

(56) References Cited

U.S. PATENT DOCUMENTS

| | | | | |
|---|---|---|---|---|
| 7,011,213 | B2* | 3/2006 | Clark | A61B 46/10 |
| | | | | 206/305 |
| 10,816,124 | B2* | 10/2020 | Molineux | F16K 3/30 |
| 2014/0216963 | A1* | 8/2014 | Whitney | G03B 17/56 |
| | | | | 383/207 |
| 2015/0169089 | A1* | 6/2015 | Dixon | B05D 1/30 |
| | | | | 427/256 |
| 2019/0314105 | A1* | 10/2019 | Zwierstra | A61B 46/10 |

* cited by examiner

COVERING FOR AN ELECTRONIC IMAGING DEVICE

RELATED APPLICATION

This application claims priority to U.S. Provisional Patent Application No. 62/902,436, filed Sep. 19, 2019, which is incorporated herein by reference.

FIELD OF THE INVENTION

The present disclosure generally relates to a covering for an electronic imaging device. More particularly, the present invention is directed to a covering for an electronic imaging device with an optically transparent display screen viewing window for being adhered to a display screen of an electronic imaging device and a band bag sleeve of flexible sheet material that cooperates with the display screen viewing window to envelop the electronic imaging device thereby creating a sterile barrier between the electronic imaging device and a surrounding environment.

BACKGROUND OF THE INVENTION

In hospitals, clinics, and other medical facilities where sterile procedures are performed, coverings can be employed to cover equipment to create a substantially sterile environment. It is known, for example, to use sterile band bags, plastic bags with elastic openings, to drape over equipment to create a sterile operating field. Such overlying coverings can be used on many types of equipment, including video and computer monitors, touch screens, liquid crystal displays, and other electronic imaging, viewing, and control devices.

Disadvantageously, while useful in achieving a sterile environment, sterile band bags according to the prior art do not provide the optical clarity required to properly view and operate many video and computer monitors, touch screens, liquid crystal displays, and other electronic imaging, viewing, and control devices optimally and in accordance with diagnostic medical imaging standards. For example, current sterile band bags are known to be thick and cloudy, and they are not made to fit snugly around the screens of monitors and displays. Consequently, the vision of the operator can be impaired as the operator viewing the display screen through current sterile band bags typically sees a cloudy and distorted image.

Current sterile band bags also tend to be thick and bulky and prone to inadvertent movement, such as sliding and other displacement. Such unintended movement and the awkwardness of the thick and bulky bags lead to confusion and inefficiency and create an increased risk of dangerous mistakes. Such problems and risks can be particularly apparent when an operator attempts to operate the graphical user interface of a touch screen. Actuating an incorrect button or the like, or even the possibility of doing so, as a result of poor visual perception possibly combined with an inadvertently moving covering, hinders efficient performance and increases patient risks.

It is thus apparent that there is a need in the art for a covering for electronic imaging devices that enables medical equipment having optical displays to be covered in a sterile manner while providing surgical staff with optically clear visualization of the display screen and preventing inadvertent displacement.

SUMMARY OF THE INVENTION

In view of the demonstrated need in the art, the present invention is founded on the basic object of providing a covering for electronic imaging devices that enables medical equipment having optical displays to be covered in a sterile manner while providing surgical staff with optically clear visualization of the display screen.

A further object of embodiments of the invention is to provide a covering for electronic imaging devices that prevents inadvertent displacement of the covering in relation to the medical equipment.

Another object of embodiments of the invention is to provide a covering for electronic imaging devices that promotes a sterile operating environment while permitting full and effective use of the imaging device and related medical equipment.

Still another object of embodiments of the invention is to provide a covering for electronic imaging devices that prevents confusion and inefficiency while minimizing the risk of mistakes due to obscured visual perception and unintended movement.

These and further objects and advantages of embodiments of the invention will become obvious not only to one who reviews the present specification but also to one who has an opportunity to make use of an embodiment of the covering for electronic imaging devices disclosed herein. It will be appreciated that, while the accomplishment of each of the foregoing objects in a single embodiment of the invention may be possible and indeed preferred, not all embodiments will seek or need to accomplish each and every potential object and advantage. Nonetheless, all such embodiments should be considered within the scope of the invention.

In carrying forth one or more objects of the invention, an embodiment of the covering for electronic imaging devices has a band bag sleeve of flexible material. The band bag sleeve terminates in a mouth. A display screen viewing window, which is formed from an optically transparent material, is centrally disposed in the band bag sleeve. The display screen viewing window has an inner surface, an outer surface, and a peripheral edge. The peripheral edge of the display screen viewing window is joined to the band bag sleeve in a sealed manner, and the display screen viewing window is sized and shaped in correspondence to the display screen of the electronic imaging device. An adherent is retained by the inner surface of the display screen viewing window, and the adherent is operative to affix the display screen viewing window to the display screen of the electronic imaging device. A release liner can be removably adhered to the inner surface of the display screen viewing window prior to application of the covering to an electronic imaging device.

Under the foregoing construction, the band bag sleeve and the display screen viewing window together define an inner volume contiguous with the mouth for receiving and enveloping at least a portion of the electronic imaging device. The covering can be applied to envelop the at least a portion of the electronic imaging device within the inner volume, and the display screen viewing window can be adhered to the display screen. A sterile barrier is thus created between the portion of the electronic imaging device within the inner volume of the covering and an environment exterior to the inner volume while permitting optically clear, stable viewing and operation of the display screen.

The band bag sleeve and the display screen viewing window are formed from a material capable of being sterilized. In certain practices, the band bag sleeve is formed from a plastic sheet material, such as polyethylene or polypropylene sheet material. The display screen viewing window can comprise a planar panel. For instance, the display screen viewing window can be formed from an optically clear, distortion free plastic, such as but not limited to an acetate film or a polyurethane film. The display screen viewing window is, in preferred embodiments, visibly distinct from the band bag sleeve.

As disclosed herein, the mouth of the band bag sleeve can be disposed generally opposite to the display screen viewing window, and the covering can further include a cinching mechanism, such as elastic banding, a drawstring, or another cinching mechanism, disposed to traverse the mouth of the band bag sleeve. The cinching mechanism is operative to constrict the mouth of the band bag sleeve thereby to further enclose the electronic imaging device.

The adherent retained by the inner surface of the display screen viewing window could comprise static electricity. Alternatively or additionally, the adherent retained by the inner surface of the display screen viewing window can comprise adhesive disposed on the inner surface of the display screen viewing window. The adhesive can be an optically clear adhesive, such as an optically clear acrylic adhesive. The adherent can be disposed in a band over the periphery of the inner surface, over substantially the entire inner surface, or otherwise.

The covering so disclosed can be employed to practice a method for enveloping an electronic imaging device with a covering. The method can be founded on providing a covering comprising a band bag sleeve of flexible material wherein the band bag sleeve terminates in a mouth; a display screen viewing window centrally disposed in the band bag sleeve wherein the display screen viewing window is formed from an optically transparent material, wherein the display screen viewing window has an inner surface, an outer surface, and a peripheral edge, wherein the peripheral edge of the display screen viewing window is joined to the band bag sleeve in a sealed manner, and wherein the display screen viewing window is sized and shaped in correspondence to the display screen of the electronic imaging device whereby the band bag sleeve and the display screen viewing window together define an inner volume contiguous with the mouth for receiving and enveloping at least a portion of the electronic imaging device; and an adherent retained by the inner surface of the display screen viewing window. With such a covering provided, at least a portion of the electronic imaging device including a display screen can be caused to be received through the mouth and into the inner volume of the covering defined by the band bag sleeve and the display screen. The display screen viewing window can be adhered to the display screen of the electronic imaging device whether before or after the electronic imaging device is received through the mouth and into the inner volume. With the covering so applied, a barrier is created between the at least a portion of the electronic imaging device within the inner volume and an environment exterior to the inner volume while permitting optically clear, stable viewing and operation of the display screen.

Where the covering further includes a cinching mechanism that is operative to constrict the mouth of the band bag sleeve, the method can further comprise constricting the cinching mechanism after the step of causing at least a portion of the electronic imaging device including a display screen to be received through the mouth and into the inner volume of the covering defined by the band bag sleeve and the display screen. Furthermore, where the covering further comprises a release liner removably adhered to the inner surface of the display screen viewing window, the method can further include the step of removing the release liner from the inner surface of the display screen viewing window prior to the step of adhering the display screen viewing window to the display screen of the electronic imaging device.

In certain practices of the invention, the steps of causing at least a portion of the electronic imaging device including a display screen to be received through the mouth and into the inner volume of the covering defined by the band bag sleeve and the display screen and adhering the display screen viewing window to the display screen of the electronic imaging device can be carried out by disposing the covering in an inside-out condition with what will ultimately be the inner surface of the viewing window exposed, aligning the display screen viewing window with the display screen, adhering the display screen viewing window with the display screen, and then adjusting the covering from the inside-out configuration to a configuration wherein the covering envelops the at least a portion of the electronic imaging device by causing the mouth to pass over the at least a portion of the electronic imaging device. Moreover, where the covering further comprises a cinching mechanism operative to constrict the mouth of the band bag sleeve, the method can further comprise the step of constricting the cinching mechanism after the step of adjusting the covering from the inside-out configuration to a configuration wherein the covering envelops the at least a portion of the electronic imaging device by causing the mouth to pass over the at least a portion of the electronic imaging device.

One will appreciate that the foregoing discussion broadly outlines the more important features of the invention merely to enable a better understanding of the detailed description that follows and to instill a better appreciation of the inventor's contribution to the art. Before an embodiment of the invention is explained in detail, it must be made clear that the following details and descriptions of inventive concepts are mere examples of the many possible manifestations of the invention.

BRIEF DESCRIPTION OF THE DRAWINGS

The foregoing and other objects, features, and advantages of the devices, systems, and methods described herein will become apparent from the following description of particular embodiments of the invention in conjunction with the accompanying drawings. It will be understood that the drawings are not necessarily to scale, emphasis instead being placed upon illustrating the principles of the devices, systems, and methods described herein.

In the drawings, like reference numerals identify corresponding elements, wherein.

DETAILED DESCRIPTION OF PREFERRED EMBODIMENTS

The covering for an electronic imaging device disclosed herein is subject to varied embodiments, each within the scope of the invention. However, to ensure that one skilled in the art will be able to understand and, in appropriate cases, practice the present invention, certain preferred embodiments of the broader invention revealed herein are described below.

Figure 1A:
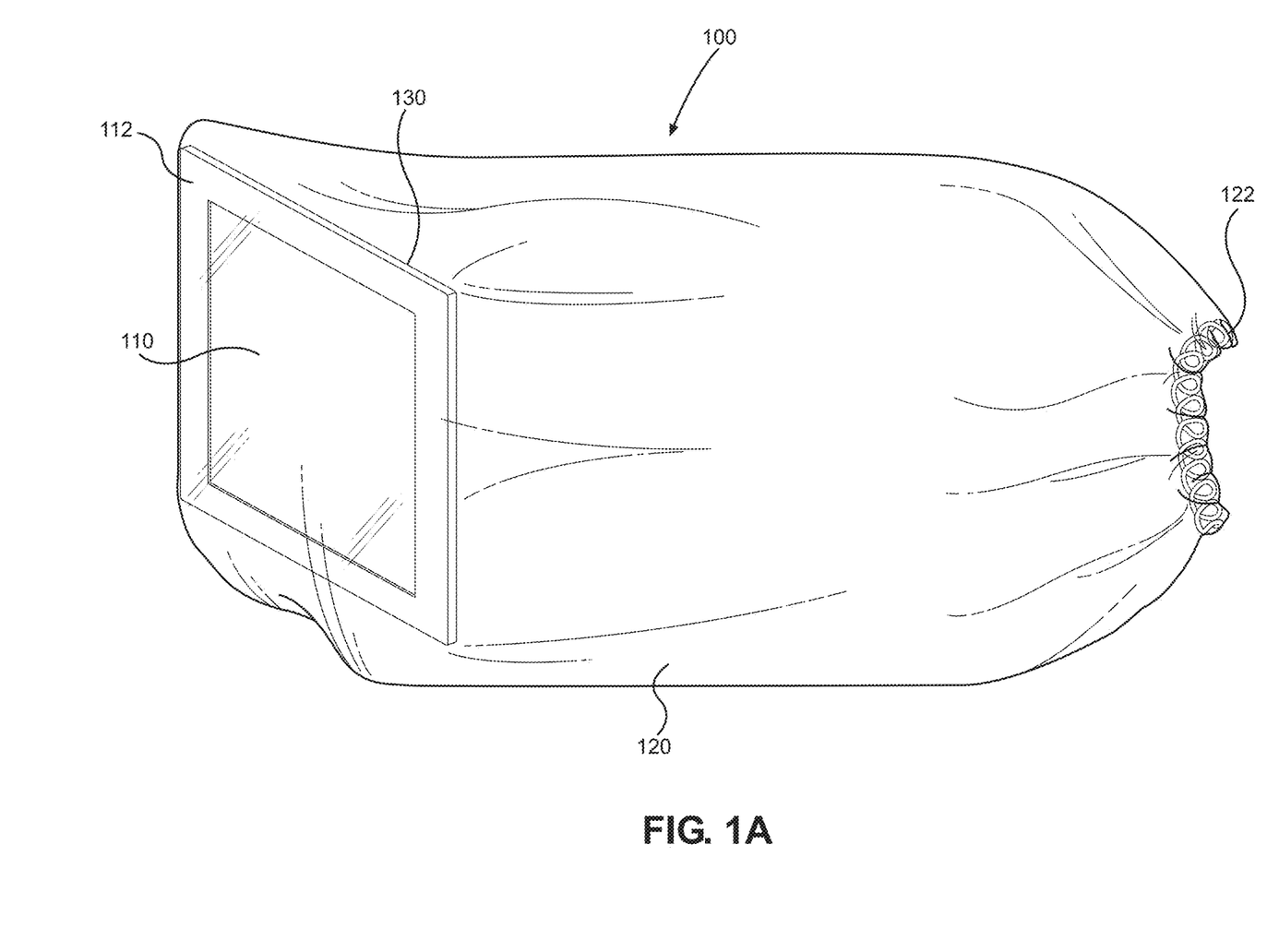
FIG. 1A is a perspective view of a covering for an electronic imaging device as disclosed herein.
Figure 1B:
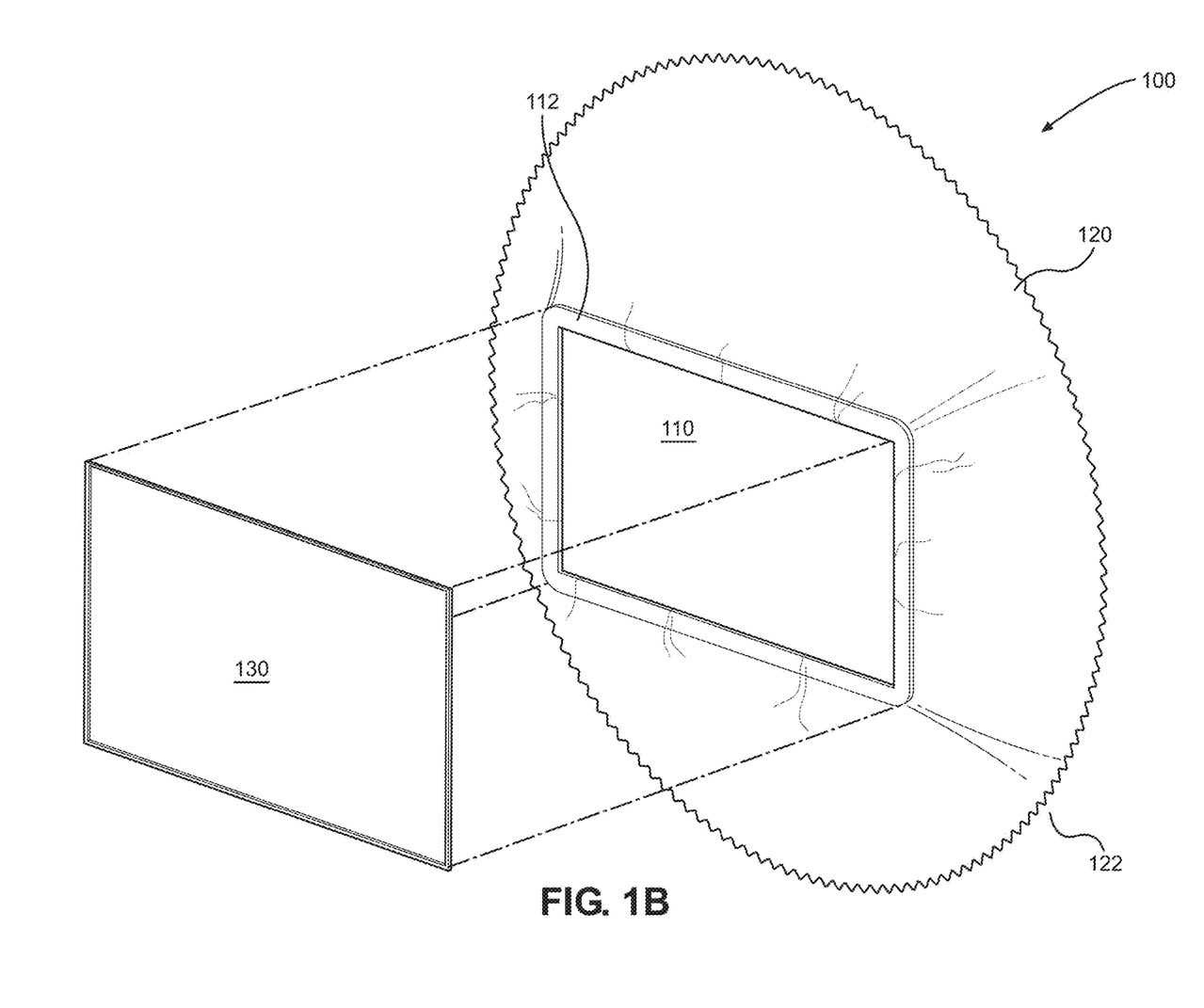
FIG. 1B is a rearward perspective view of a covering for an electronic imaging device according to the invention in a splayed configuration.
Figure 2:
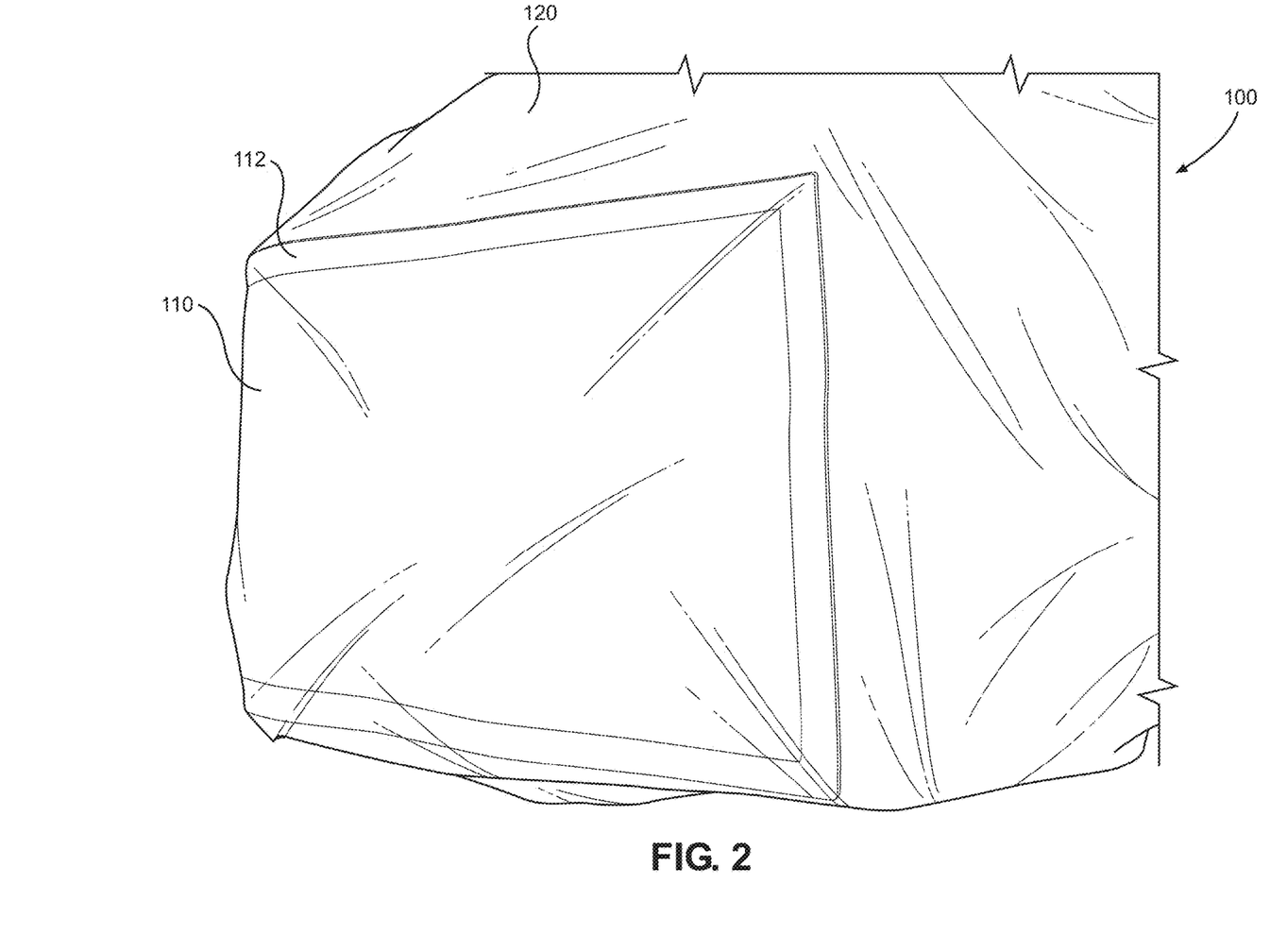
FIG. 2 is a top plan view of the covering for an electronic imaging device according to the invention prepared for application to an electronic device.
Figure 3:
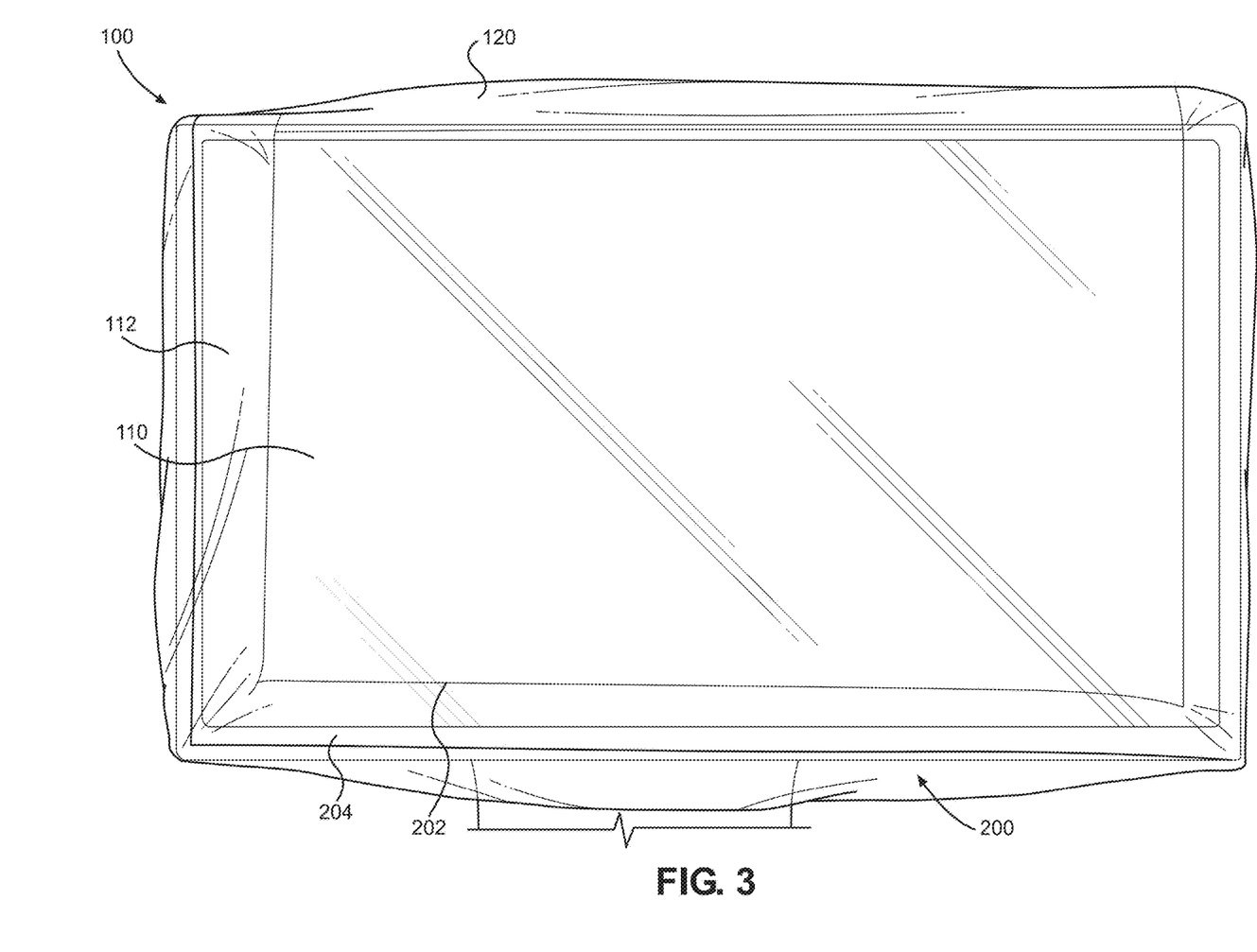
FIG. 3 is a view in front elevation of the covering for an electronic imaging device as applied to the electronic device.
Figure 4:
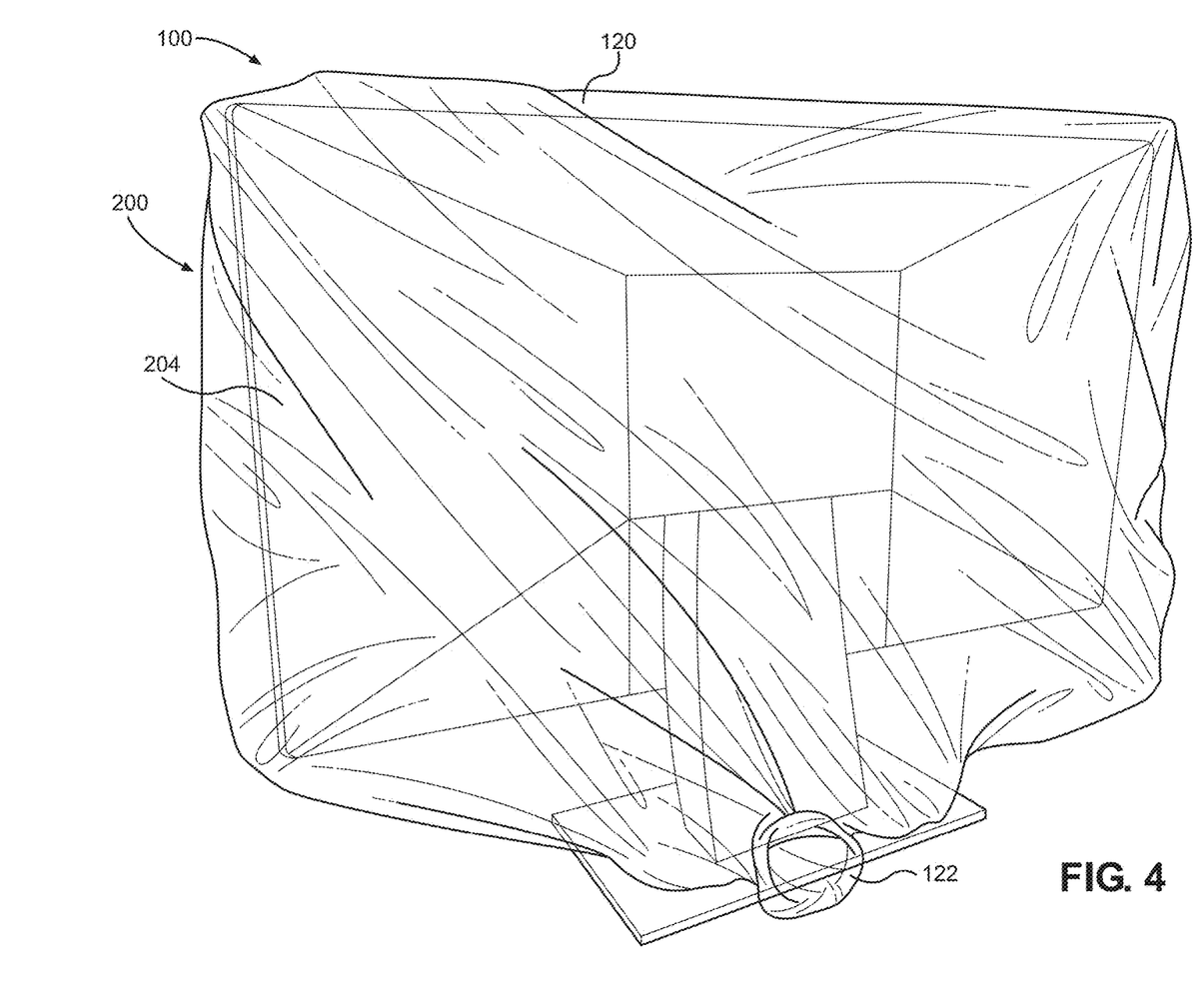
FIG. 4 is a rearward perspective view of the covering for an electronic imaging device as applied to the electronic device.
Figure 5:
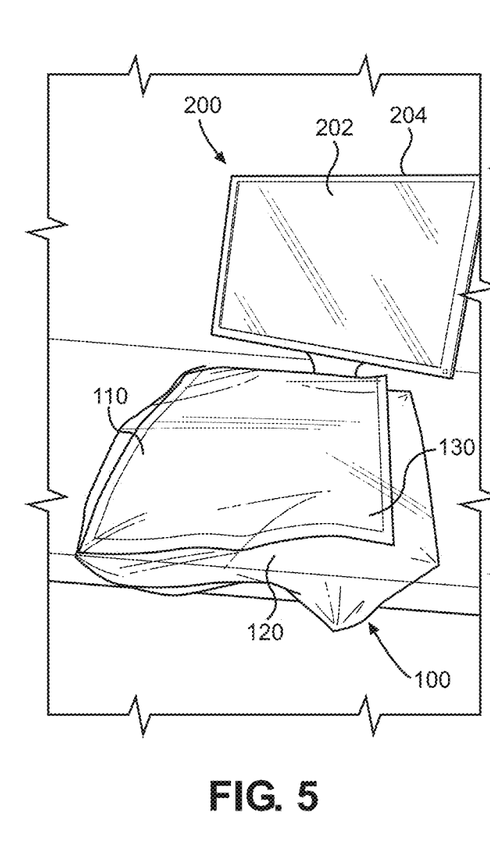
FIG. 5 is a perspective view of the covering for an electronic imaging device with a protective membrane prior to application to the electronic imaging device.
Figure 6:
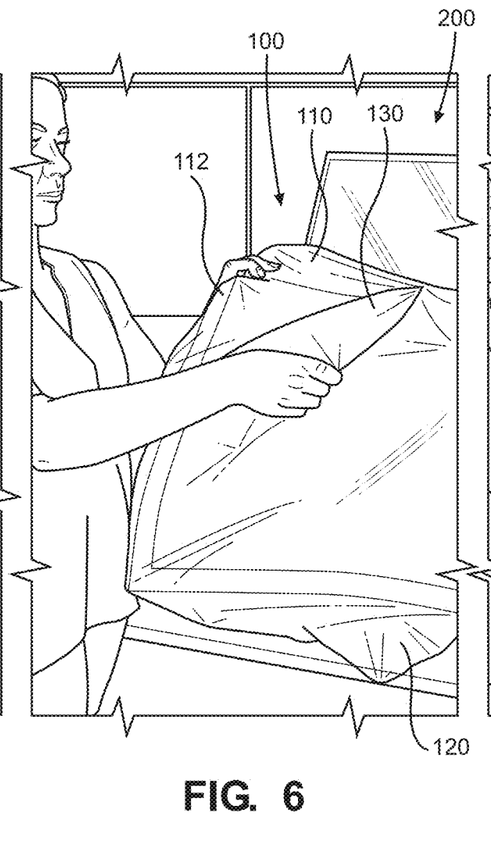
FIG. 6 is a perspective view of the covering for an electronic imaging device during removal of the protective membrane.
Figure 7:
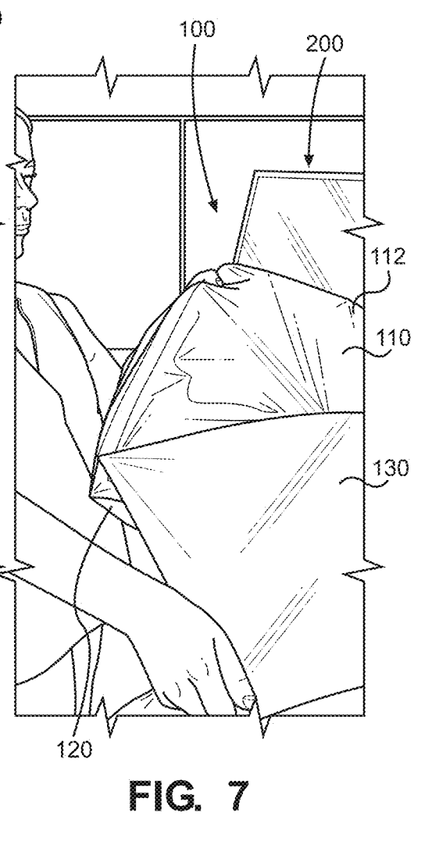
FIG. 7 is a perspective view of the covering for an electronic imaging device during a further stage of removal of the protective membrane.
Figure 8:
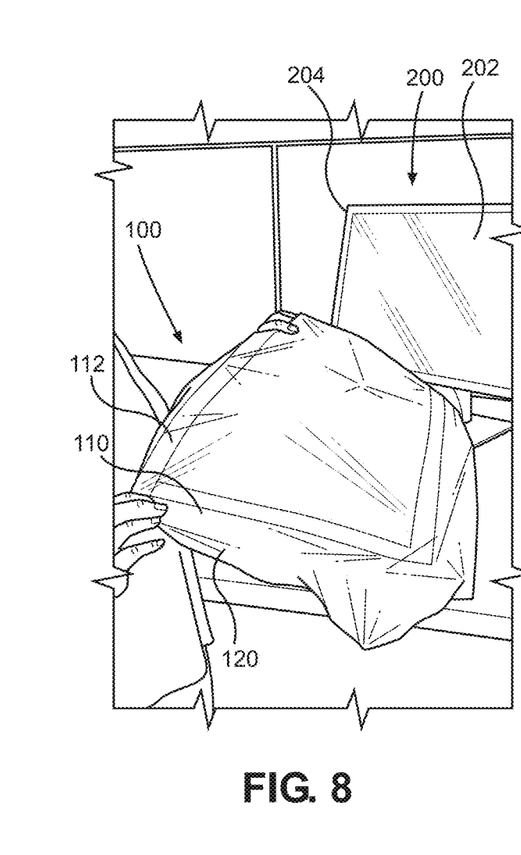
FIG. 8 is a perspective view of the covering for an electronic imaging device with the protective membrane fully removed.
Figure 9:
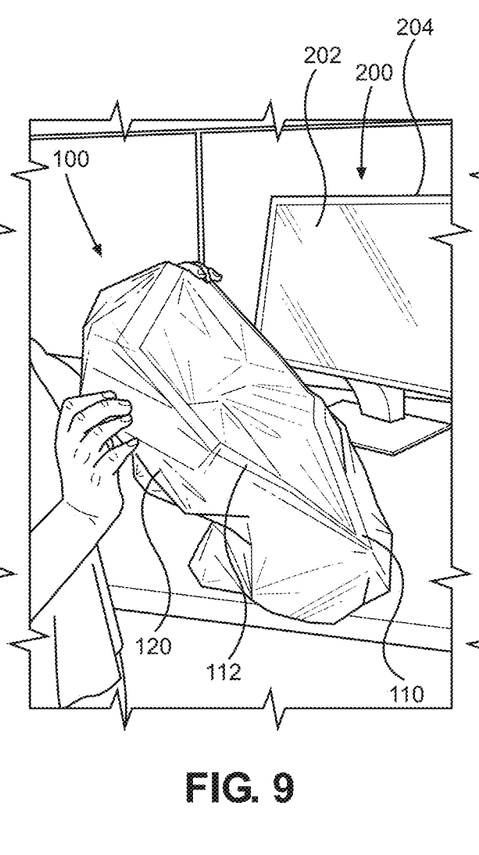
FIG. 9 is a perspective view of the covering for an electronic imaging device during alignment for engagement with the electronic imaging device.
Figure 10:
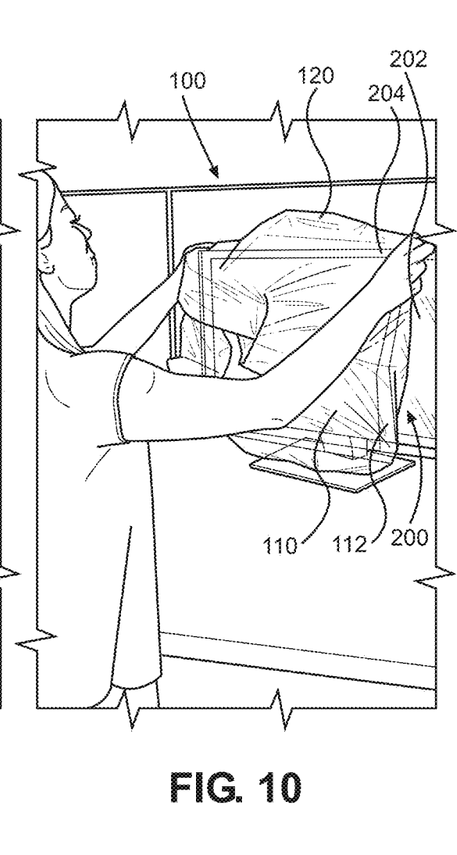
FIG. 10 is a perspective view of the covering for an electronic imaging device aligned for engagement with the electronic device.
Figure 11:
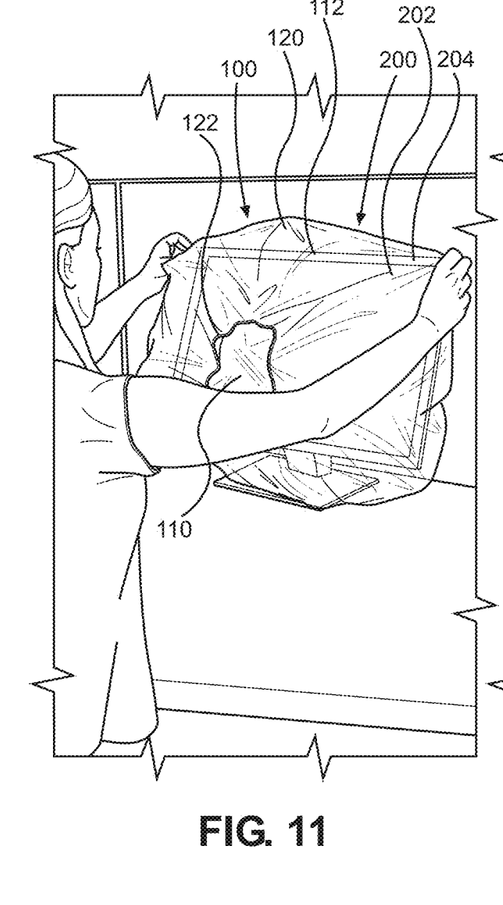
FIG. 11 is a perspective view of the covering for an electronic imaging device with the display screen window being engaged with the electronic imaging device.
Figure 12:
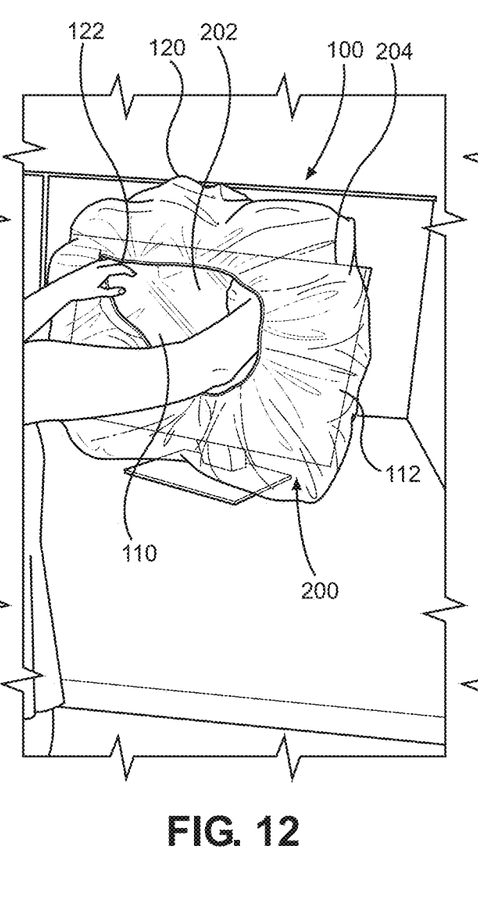
FIG. 12 is a perspective view of the covering for an electronic imaging device with the display screen window during a further stage of engagement with the electronic imaging device.
Figure 13:
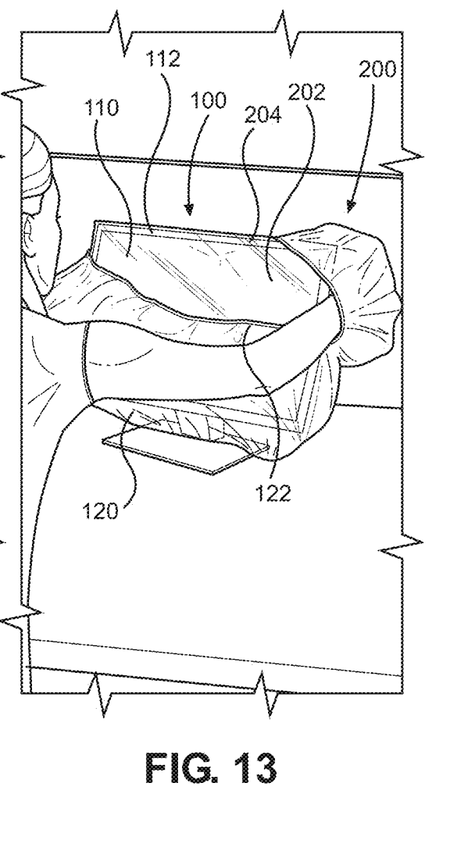
FIG. 13 is a perspective view of the covering for an electronic imaging device with the display screen window engaged with the electronic imaging device and with the sterile bag portion being draped over the electronic imaging device.
Figure 14:
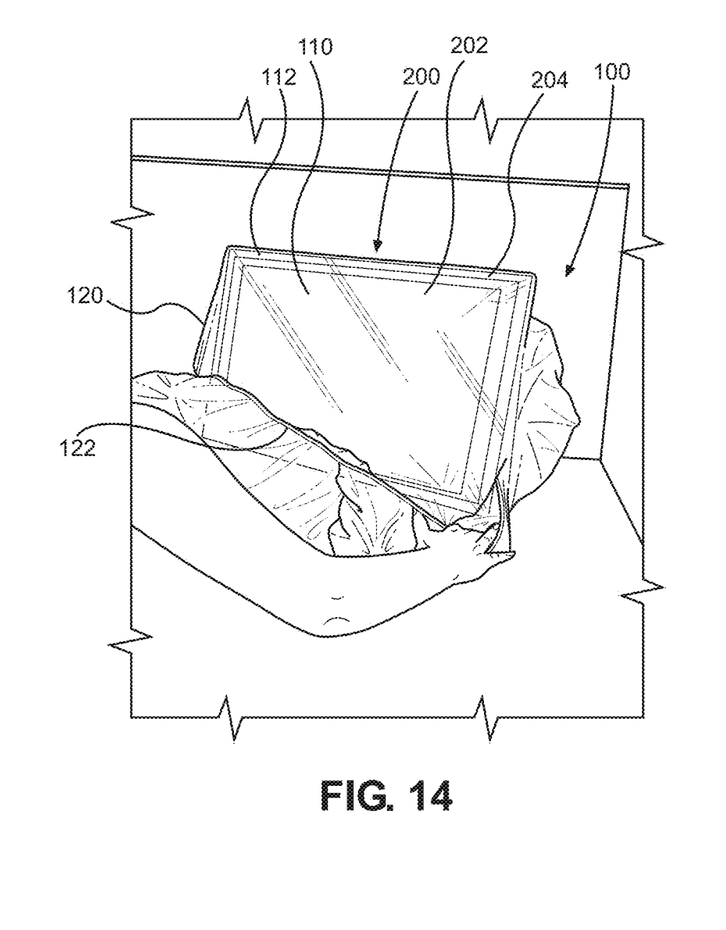
FIG. 14 is a perspective view of the covering for an electronic imaging device with the sterile bag portion in a further stage of being draped over the electronic imaging device.
Figure 15:
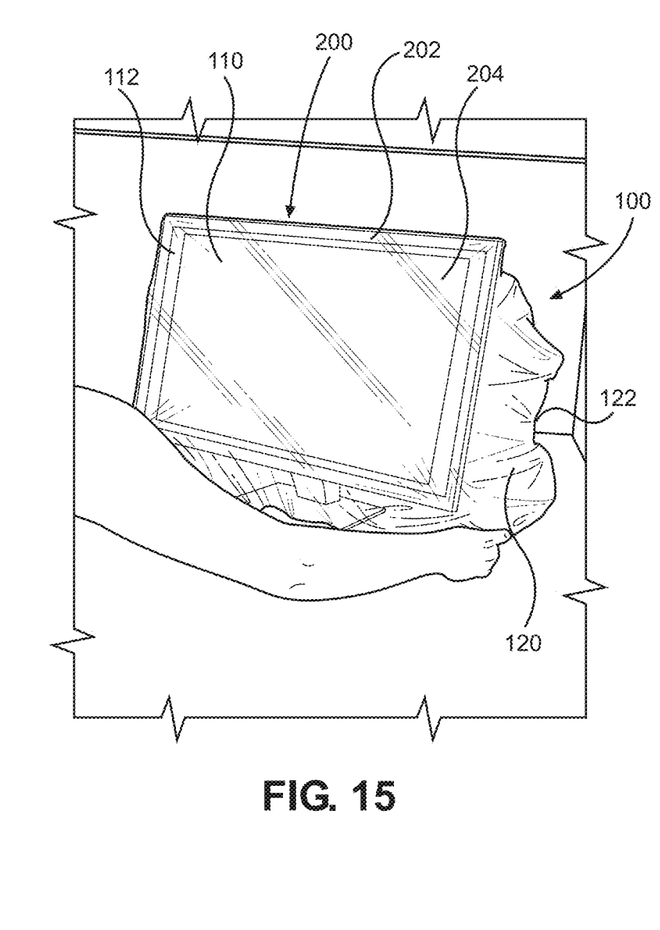
FIG. 15 is a perspective view of the covering for an electronic imaging device with the sterile bag portion fully draped over the electronic imaging device.

Turning more particularly to the drawings, a covering for an electronic imaging device is indicated generally at 100 in FIGS. 1A through 17. There, the covering 100 has a sterile band bag sleeve 120 for enveloping an electronic imaging device 200 as shown in FIG. 3, for instance. There, the electronic imaging device 200 can be seen to have a display screen 202 for displaying text and images. In certain instances, the display screen 202 may be operable to enable, among other things, data input, touchscreen operation of the electronic imaging device 200 and, additionally or alternatively, control over associated medical equipment. As described further hereinbelow, the covering 100 for the electronic imaging device 200 has a display screen viewing window 110 centrally disposed within the band bag sleeve 120 for being aligned with and adhered to the display screen 202 of the electronic imaging device 200.

Under this briefly-described construction, the covering 100 can be applied to an electronic imaging device 200 as in FIG. 3 to enable optically clear perception of the display screen 202 and, as applicable, stable control over a graphical user interface disposed thereon. In non-limiting applications of the invention, the covering 100 can be applied to electronic imaging devices 200 disposed in a substantially sterile environment, such as a medical facility or a laboratory. The electronic imaging device 200 may also or instead be disposed in other locations where the electronic imaging device 200 is susceptible to damage, contamination, or debris so that a covering 100 as described herein may be advantageous for protecting the electronic imaging device 200.

According to embodiments of the invention, the band bag sleeve 120 can be formed from a sterile flexible material or from a lamination of sterile, flexible materials. By way of example and not limitation, the band bag sleeve 120 could be formed from flexible plastic sheeting, from sterile paper, or from any other sterile, flexible material effective in use as a sterile drape. Also within the scope of the invention, the band bag sleeve 120 could be formed with multiple layers of similar or different materials, such as multiple layers of plastic sheeting, of layers of paper and plastic sheeting, or of some other combination of layers of material. One or more of the layers of the band bag sleeve 120 can be liquid-impermeable. In one non-limiting practice of the invention, the band bag sleeve 120 is formed from low-density polyethylene, polypropylene, or another plastic sheet material can be sterilized. The band bag sleeve 120 can be translucent or opaque. For instance, where the band bag sleeve 120 is formed from plastic sheeting, it can be translucent.

Together, the band bag sleeve 120 and the display screen viewing window 110 define an inner volume with a mouth disposed at a terminal edge of the band bag sleeve 120 generally opposite to the viewing window 110. A cinching mechanism 122 traverses the mouth. The cinching mechanism 122 can, by way of example and not limitation, comprise elastic banding, a drawstring, or some combination thereof. As such, when the covering 100 is applied to envelop the article of imaging equipment 200, the article of equipment 200 is received through the mouth. In the case of elastic banding as the cinching mechanism 122, the cinching mechanism 122 can automatically constrict the mouth of the band bag sleeve 120 and the covering 100 in general, such as upon itself or upon any protruding portion of the article of equipment 200, such as wiring, a support arm, or some other protruding aspect as in FIG. 4. Where the cinching mechanism 122 comprises a drawstring or other selectively operable cinching mechanism, the cinching mechanism 122 can be selectively constricted. When the article of imaging equipment 200 is received into the inner volume of the covering 100 and when the cinching mechanism 122 is caused or permitted to constrict to a narrowed condition, the article of imaging equipment 200 is protectively encased.

The sterile band bag sleeve 120 is sufficient in size to envelop at least the monitor or other portion of the article of medical equipment 200 retaining the display screen 202. Accordingly, when the covering 100 is applied to envelop the article of equipment 200, a sterile environment is facilitated. The patient is protected against contamination from the article of equipment 200, and the article of equipment 200 is protected against contamination due to exposure to the relevant medical procedure.

As set forth above, the covering 100 for the electronic imaging device 200 has a display screen viewing window 110 centrally disposed to span an aperture in the band bag sleeve 120. When the covering 100 is applied to the electronic imaging device 200, the display screen viewing window 110 can be aligned with the display screen 202 of the electronic imaging device 200 as, for instance, in FIG. 3.

The viewing window 110 is planar and can be sized and shaped in correspondence to the size and shape of the display screen 202 of the electronic imaging device 200. For example, a perimeter of the viewing window 110 may correspond to a perimeter of the display screen 202 of the electronic imaging device 200. In certain implementations, the viewing window 110 is substantially rectangular to conform in shape with a rectangular display screen 202 of the electronic imaging device 200. The viewing window 110 can be sized and shaped to cover an entirety of the front portion of an electronic imaging device 200, which may consist of or include the display screen 202 and an anterior framework 204. The viewing window 110 comprises a planar sheet of material that corresponds to the size and shape of the display screen 202 or the entire front portion of the electronic imaging device 200 including a framework 204 surrounding the display screen 202.

The viewing window 110 comprises an optically transparent panel that can be sterilized. For instance, the viewing window 110 can be formed from an optically clear plastic film or panel that can be flexible, semi-rigid, or rigid. The viewing window 110 is preferably crafted from a material that allows a user to interact with a touchscreen of an electronic imaging device 200 through the viewing window 110. Without limitation, the viewing window 110 can be crafted from an acetate film, a polyurethane film, or another optically clear, distortion free plastic film. The viewing window can have a surface finish, such as an anti-glare, glossy, or matte finish. The display screen viewing window 110 is of a material different in type or character than the material of the sleeve portion 120. In view of the optically transparent nature of the display screen viewing window 110 as compared to the surrounding band bag sleeve 120, which may be translucent or opaque, the display screen viewing window 110 is visibly distinct from the band bag sleeve 120.

The viewing window 110 and the portion of the band bag sleeve 120 bordering the viewing window 110 are bonded together in a liquid-impermeable manner. Bonding could be carried out in a number of ways within the scope of the invention, including by adhesive, by heat sealing, by ultrasonic welding, by solvent welding, or by some other method or combination of methods. When bonded together, the sleeve portion 120 and the viewing window 110 form a unitary, sealed structure.

The viewing window 110 has an inner surface disposed to face toward the interior volume of the band bag sleeve 120 and an outer surface. The viewing window 110 and the covering 100 in general can be selectively fixed in relation to the display screen 202 and the electronic imaging device 200 in general. In certain embodiments, the viewing window 110 can be removably and replaceably fixed to the display screen 202, such as by static electricity, by a pressure sensitive adhesive 112 that is ideally removable without adhesive residue, or by some other method or combination of methods. Where the adherent comprises static electricity, it can be formed at least in part by an electric charge within or on the material of the viewing window 110. In preferred embodiments, a fastening adhesive 112 comprises a layer of optically clear adhesive, such as an optically clear acrylic adhesive. The fastening adhesive 112 can be disposed in a band along the perimeter of the viewing window 110. In other practices, the fastening adhesive 112 is disposed over the entire inner surface of the viewing window 110 whereby the entire contacting surfaces of the viewing window 110 and the display screen 202 are actively adhered to one another.

Prior to use and application of the covering 100, a release liner 130, such as a panel of polyester plastic, a plasticized paper, or some other type of release material, is removably adhered to the inner surface of the viewing window 110 for protecting the inner surface against contamination, loss of adhesion, and inadvertent adhesion. As described herein, the release liner 130 can be removed at a desired stage of application of the covering 100 to an electronic imaging device 200.

The band bag sleeve 120 and the display screen viewing window 110 cooperate to define an interior volume with the mouth bounded by the cinching mechanism 122 providing an entrance thereto for receiving an electronic imaging device 200 to be encased by the covering 100. Once the electronic imaging device 200 is received into the inner volume of the covering 100 and the display screen viewing window 110 is affixed to the display screen 202 as described herein, the cinching mechanism 122 can be caused or allowed to constrict the mouth thereby to substantially close the received portion of the electronic imaging device 200 within the inner volume of the covering 100 while providing a constricted passage as necessary for support structures, wiring, and other necessary components.

Figure 16:
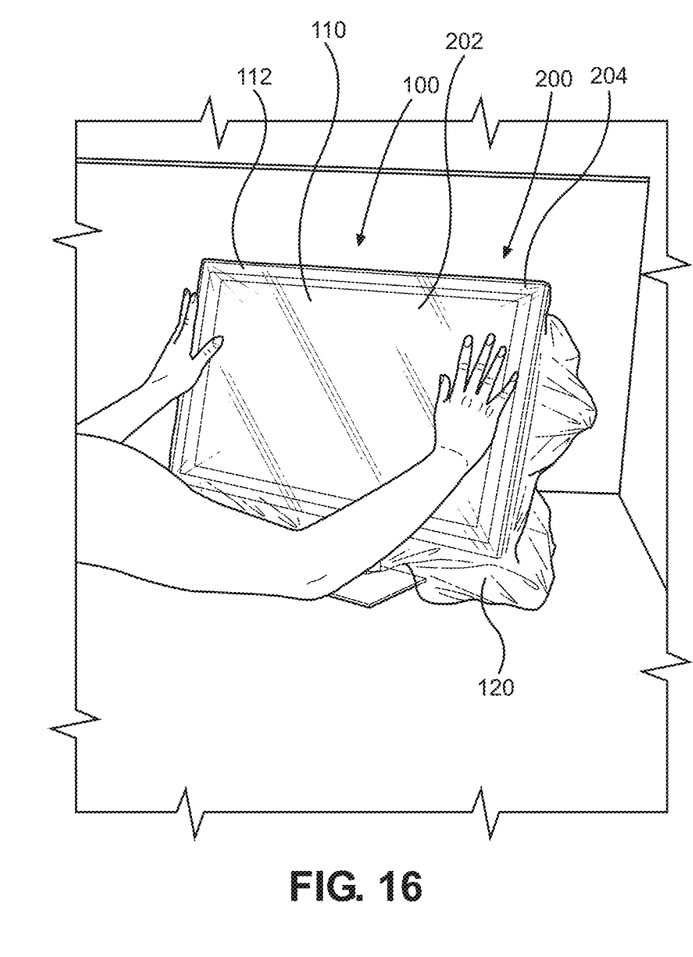
FIG. 16 is a perspective view of the covering for an electronic imaging device during further application of the display screen window to the display screen of the electronic device.
Figure 17:
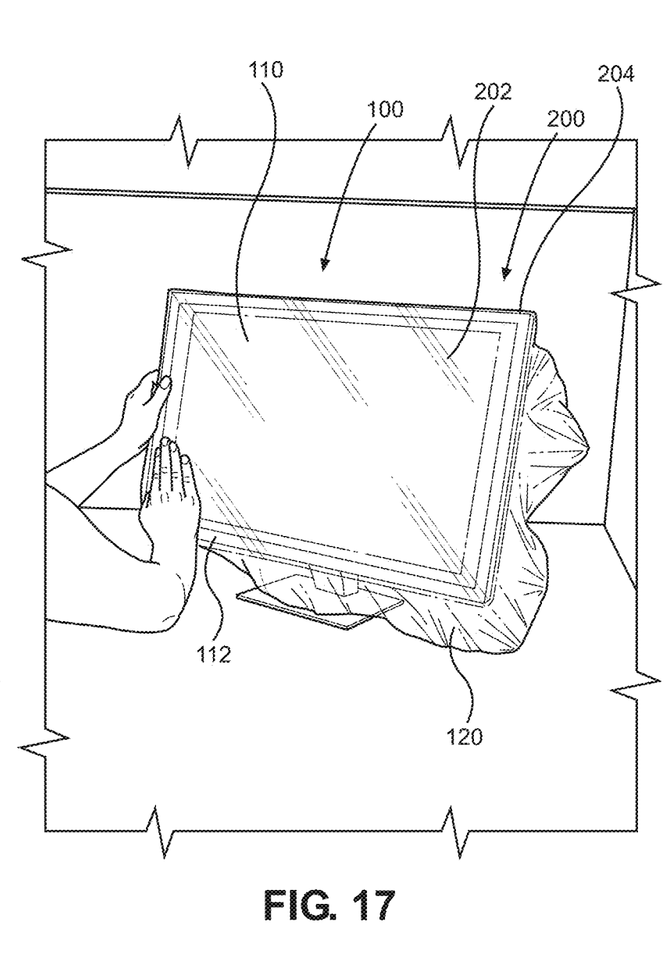
FIG. 17 is a perspective view of the covering for an electronic imaging device during still further application of the display screen window to the display screen of the electronic imaging device.

The covering 100 so disclosed can be employed to practice a method for creating a sterile barrier between an electronic imaging device 200 and a surrounding environment, the steps of that method being understood with particular reference to FIGS. 5 through 17. In the depicted example, the electronic imaging device 200 comprises a computer monitor electronic imaging device 200, but the invention is not so limited. The method can began with the providing of a covering 100 as taught herein with a band bag sleeve 120 and a centrally disposed, optically transparent display screen viewing window 110 retaining a removable release liner 130 on its inner surface. At a desired stage of the method, whether before receiving the electronic imaging device 200 into the inner volume of the covering 100 or after, the release liner 130 can be removed, such as by peeling, from the inner surface of the display screen viewing window 110 as in the progressive depictions of FIGS. 6 and 7. Where, as in the stages of FIGS. 6 and 7, the release liner 130 is removed prior to disposing the electronic imaging device 200 into the inner volume of the covering 100, the covering 100 can be disposed in an inside-out condition with what will ultimately be the inner surface of the viewing window 110 exposed and the band bag sleeve 120 trailing therebehind. The covering 100 can then be gripped, such as by gripping the covering 100 adjacent to the edges of the exposed inner surface of the viewing window 110 as in FIGS. 8 and 9. Then, the viewing window 110 can be aligned with the user interface of the display screen 202 of the electronic imaging device 200 and pressed into facing contact therewith as in FIGS. 10 and 11. By operation of the adherent nature of the inner surface of the viewing window 110, whether by adhesive 112 disposed about the periphery of the window 110 or over the entire window 110, by static clinging force, or by another method or combination thereof. With the display screen viewing window 110 fixed in place protecting the display screen 202, the band bag sleeve 120 can then be adjusted from its inside-out configuration anterior to the display screen 202 to its working configuration to receive and envelop the portion of the electronic imaging device 200 to be encased. The computer monitoring wiring and any other protruding aspects, such as a support or other aspect, are passed through the mouth defined by the cinching mechanism 122 as shown in the final configurations of FIGS. 3 and 4. With the covering 100 so disposed, the display screen viewing window 110 can, if and as necessary, be pressed and smoothed into full facing contact with the display screen 202 as shown in FIGS. 16 and 17.

By application of the covering 100 to the electronic imaging device 200 as disclosed herein, the electronic imaging device 200 is safely encased within the covering 100 with the cinching mechanism 122 constricting the mouth of the covering 100 to create an enclosed inner volume. A sterile barrier is thus created between the electronic imaging device 200 and the exterior environment while offering medical staff optically-correct visual clarity to view medical images, information, and other graphics displayed on the display screen 202 of the electronic imaging device 200 without obstruction or distortion. Moreover, where applicable, touchscreen capabilities are maintained, and touchscreens can be actuated with an improved tactile feel while remaining as accurately reactive as if no covering 100 were in place. By the adhesion of the display screen viewing window 110 to the display screen 202, inadvertent displacement of the covering in relation to the electronic imaging device 200 is prevented. The risks of distortions and failures in clarity and the inefficiencies and compromises in performance attendant to makeshift covering methods of the prior art are eliminated. The display screen viewing window 110 can be readily applied to video monitors, computer touch screens, liquid crystal displays, and other electronic imaging devices 200 in a rapid and convenient manner to create a sterile environment. The clear, optically correct viewing window 110 and the covering 100 in general can be installed as part of the draping process. The peel-back nature of the release liner 130 permits the separation of the liner 130 from the viewing window 110 in seconds to allow the operator to attach the film or other material of the viewing window 110 to the display screen 202 of the electronic imaging device 200 during the sterile draping process.

As used herein, references to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, for example, the term "or" should generally be understood to mean "and/or."

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments. Where ranges of values are provided, they are also intended to include each value within the range as if set forth individually, unless expressly stated to the contrary. The use of any and all examples, or exemplary language, as in "such as" or the like, provided herein, is intended merely to better illuminate the embodiments and does not pose a limitation on the scope of the embodiments. No language in the specification should be construed as indicating any unclaimed element as essential to the practice of the embodiments. In the description, it is understood that terms such as "first," "second," "top," "bottom," "upper," "lower," and the like, are words of convenience and are not to be construed as limiting terms.

With certain details and embodiments of the present invention for a covering for an electronic imaging device disclosed, it will be appreciated by one skilled in the art that numerous changes and additions could be made thereto without deviating from the spirit or scope of the invention. This is particularly true when one bears in mind that the presently preferred embodiments merely exemplify the broader invention revealed herein. Accordingly, it will be clear that those with major features of the invention in mind could craft embodiments that incorporate those major features while not incorporating all of the features included in the preferred embodiments. In addition, the order or presentation of method steps in the description and drawings is not intended to require this order of performing the recited steps unless a particular order is expressly required by the claims.

Therefore, the following claims shall define the scope of protection to be afforded to the invention. Those claims shall be deemed to include equivalent constructions insofar as they do not depart from the spirit and scope of the invention. It must be further noted that a plurality of the following claims may express, or be interpreted to express, certain elements as means for performing a specific function, at times without the recital of structure or material. As the law demands, any such claims shall be construed to cover not only the corresponding structure and material expressly described in this specification but also all legally cognizable equivalents thereof.

I claim as deserving the protection of Letters Patent:

1. A covering for an electronic imaging device with a display screen, the covering comprising:
    a band bag sleeve of flexible material wherein the band bag sleeve terminates in a mouth;
    a display screen viewing window comprising a planar sheet of material centrally disposed in the band bag sleeve wherein the display screen viewing window is formed from an optically transparent material, wherein the display screen viewing window has an inner surface, an outer surface, and a peripheral edge, wherein the peripheral edge of the display screen viewing window is joined to the band bag sleeve in a sealed manner, and wherein the display screen viewing window is sized and shaped in correspondence to the display screen of the electronic imaging device;
    a release liner removably adhered to the inner surface of the display screen viewing window wherein the release liner is adapted to be removed from the inner surface of the display screen viewing window at a stage of application of the covering to an electronic imaging device;
    an adherent retained by the inner surface of the display screen viewing window wherein the adherent is operative to affix the display screen viewing window to the display screen of the electronic imaging device;
    whereby the band bag sleeve and the display screen viewing window together define an inner volume contiguous with the mouth for receiving and enveloping at least a portion of the electronic imaging device and whereby the covering can be applied to envelop the at least a portion of the electronic imaging device within the inner volume and wherein the display screen viewing window can be adhered to the display screen whereby a barrier is created between the portion of the electronic imaging device within the inner volume and an environment exterior to the inner volume while permitting optically clear, stable viewing and operation of the display screen.

2. The covering of claim 1, wherein the band bag sleeve and the display screen viewing window are sterile.

3. The covering of claim 1, wherein the band bag sleeve is formed from a plastic sheet material.

4. The covering of claim 3, wherein the band bag sleeve material is formed from polyethylene or polypropylene.

5. The covering of claim 1, wherein the mouth of the band bag sleeve is disposed generally opposite to the display screen viewing window.

6. The covering of claim 1, further comprising a cinching mechanism disposed to traverse the mouth of the band bag sleeve, the cinching mechanism operative to constrict the mouth of the band bag sleeve.

7. The covering of claim 6, wherein the cinching mechanism comprises elastic banding.

8. The covering of claim 6, wherein the cinching mechanism comprises a drawstring.

9. The covering of claim 1, wherein the display screen viewing window comprises a planar panel.

10. The covering of claim 1, wherein the display screen viewing window is formed from an optically clear, distortion free plastic.

11. The covering of claim 10, wherein the display screen viewing window is formed from an acetate film.

12. The covering of claim 10, wherein the display screen viewing window is formed from a polyurethane film.

13. The covering of claim 10, wherein the display screen viewing window is visibly distinct from the band bag sleeve.

14. The covering of claim 1, wherein the adherent retained by the inner surface of the display screen viewing window comprises static electricity.

15. The covering of claim 1, wherein the adherent retained by the inner surface of the display screen viewing window comprises adhesive disposed on the inner surface of the display screen viewing window.

16. The covering of claim 15, wherein the adherent retained by the inner surface of the display screen viewing window comprises optically clear adhesive.

17. The covering of claim 16, wherein the adherent retained by the inner surface of the display screen viewing window comprises optically clear acrylic adhesive.

18. The covering of claim 15, wherein the adherent retained by the inner surface of the display screen viewing window is disposed in a band over the periphery of the inner surface.

19. The covering of claim 15, wherein the adherent retained by the inner surface of the display screen viewing window is disposed over substantially the entire inner surface.

20. A covering for an electronic imaging device with a display screen, the covering comprising:
a band bag sleeve of flexible sheet material wherein the band bag sleeve terminates in a mouth;
a display screen viewing window comprising a planar sheet of material centrally disposed in the band bag sleeve wherein the display screen viewing window is formed from an optically transparent, distortion free plastic, wherein the display screen viewing window has an inner surface, an outer surface, and a peripheral edge, wherein the peripheral edge of the display screen viewing window is joined to the band bag sleeve in a sealed manner, and wherein the display screen viewing window is sized and shaped in correspondence to the display screen of the electronic imaging device;
an adherent retained by the inner surface of the display screen viewing window wherein the adherent is operative to affix the display screen viewing window to the display screen of the electronic imaging device, wherein the adherent retained by the inner surface of the display screen viewing window comprises static electricity, and wherein the static electricity of the display screen viewing window is formed at least in part by an electric charge within or on the material of the viewing window; and
a cinching mechanism disposed to traverse the mouth of the band bag sleeve, the cinching mechanism operative to constrict the mouth of the band bag sleeve;
whereby the band bag sleeve and the display screen viewing window together define an inner volume contiguous with the mouth for receiving and enveloping at least a portion of the electronic imaging device and whereby the covering can be applied to envelop the at least a portion of the electronic imaging device within the inner volume and wherein the display screen viewing window can be adhered to the display screen whereby a barrier is created between the portion of the electronic imaging device within the inner volume and an environment exterior to the inner volume while permitting optically clear, stable viewing and operation of the display screen.

21. The covering of claim 20, wherein the display screen viewing window is formed from an acetate or polyurethane film.

22. The covering of claim 20, wherein the display screen viewing window is visibly distinct from the band bag sleeve.

23. The covering of claim 20, further comprising a release liner removably adhered to the inner surface of the display screen viewing window wherein the release liner is adapted to be removed from the inner surface of the display screen viewing window at a stage of application of the covering to an electronic imaging device.

24. A method for enveloping an electronic imaging device with a covering, the method comprising:
providing a covering comprising:
a band bag sleeve of flexible material wherein the band bag sleeve terminates in a mouth;
a display screen viewing window comprising a planar sheet of material centrally disposed in the band bag sleeve wherein the display screen viewing window is formed from an optically transparent material, wherein the display screen viewing window has an inner surface, an outer surface, and a peripheral edge, wherein the peripheral edge of the display screen viewing window is joined to the band bag sleeve in a sealed manner, and wherein the display screen viewing window is sized and shaped in correspondence to the display screen of the electronic imaging device whereby the band bag sleeve and the display screen viewing window together define an inner volume contiguous with the mouth for receiving and enveloping at least a portion of the electronic imaging device; a release liner removably adhered to the inner surface of the display screen viewing window wherein the release liner is adapted to be removed from the inner surface of the display screen viewing window at a stage of application of the covering to an electronic imaging device and an adherent retained by the inner surface of the display screen viewing window;

causing at least a portion of the electronic imaging device including a display screen to be received through the mouth and into the inner volume of the covering defined by the band bag sleeve and the display screen;

removing the release liner from the inner surface of the display screen viewing window; and adhering the display screen viewing window to the display screen of the electronic imaging device, wherein the step of removing the release liner from the inner surface of the display screen viewing window is performed prior to the step of adhering the display screen viewing window to the display screen of the electronic imaging device;

whereby a barrier is created between the at least a portion of the electronic imaging device within the inner volume and an environment exterior to the inner volume while permitting optically clear, stable viewing and operation of the display screen.

25. The method of claim 24, wherein the covering further comprises a cinching mechanism operative to constrict the mouth of the band bag sleeve and further comprising the step of constricting the cinching mechanism after the step of causing at least a portion of the electronic imaging device including a display screen to be received through the mouth and into the inner volume of the covering defined by the band bag sleeve and the display screen.

26. The method of claim 24, wherein the steps of causing at least a portion of the electronic imaging device including a display screen to be received through the mouth and into the inner volume of the covering defined by the band bag sleeve and the display screen and adhering the display screen viewing window to the display screen of the electronic imaging device are carried out by disposing the covering in an inside-out condition with what will ultimately be the inner surface of the viewing window exposed, aligning the display screen viewing window with the display screen, adhering the display screen viewing window with the display screen, and then adjusting the covering from the inside-out configuration to a configuration wherein the covering envelops the at least a portion of the electronic imaging device by causing the mouth to pass over the at least a portion of the electronic imaging device.

27. The method of claim 26, wherein the covering further comprises a cinching mechanism operative to constrict the mouth of the band bag sleeve and further comprising the step of constricting the cinching mechanism after the step of adjusting the covering from the inside-out configuration to a configuration wherein the covering envelops the at least a portion of the electronic imaging device by causing the mouth to pass over the at least a portion of the electronic imaging device.

* * * * *